United States Patent [19]

Phillips et al.

[11] Patent Number: 5,254,725
[45] Date of Patent: Oct. 19, 1993

[54] INHIBITORS OF KYNURENINASE

[75] Inventors: Robert S. Phillips; Rajesh K. Dua, both of Athens, Ga.

[73] Assignee: University of Georgia Research Foundation, Inc., Athens, Ga.

[21] Appl. No.: 689,705

[22] Filed: Apr. 18, 1991

[51] Int. Cl.$^5$ .................. C07C 229/36; A61K 31/195
[52] U.S. Cl. ..................................... 562/444; 560/39
[58] Field of Search ............... 562/444; 514/564, 563, 514/535, 538; 560/39

[56] References Cited

PUBLICATIONS

*Phillips and Dua *J. Amer. Chem. Soc.* 113:7385-7388 (1991).
Soda, K. and Tanizawa, K. (1979) Advances in Enzymology 49:1-40.
Tanizawa, K. and Soda, K. (1979) J. Biochem. 86:1199-1209.
Kishore, G. M. et al. (1984) J. Biol. Chem. 259:10669-10674.
Whitten, J. P. (1989) Tetrahedron Lett. 30:3649-3652.
Stevens, J. L. (1985) J. Biol. Chem. 260:7945-7950.
Palcic, M. et al. (1985) J. Biol. Chem. 260:5248-5251.
Hayaishi, O. (1955) in A Symposium on Amino Acid Metabolism, W. D. McElroy & H. B. Glass eds. Johns Hopkins Press Baltimore, pp. 914-929.

*Primary Examiner*—José G. Dees
*Assistant Examiner*—B. Frazier
*Attorney, Agent, or Firm*—Greenlee and Winner

[57] ABSTRACT

The present invention provides inhibitors of kynureninase having the formula

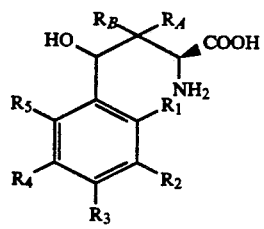

where $R_a$ and $R_b$, independently of one another are H, a halogen, $CF_3$ or a small alkyl group having one to three carbon atoms; $R_1$ is $NH_2$, $NR_6R_7$, halogen, $CF_3$ or a small alkyl group having from one to three carbon atoms, wherein $R_6$ and $R_7$, independently of one another, are H, a formyl group or a small alkyl group having from one to three carbon atoms with the exception that only one of $R_6$ or $R_7$ can be a formyl group; $R_2$ is OH, H, halogen, $CF_3$ or a small alkyl group having from one to three carbon atoms; and $R_3$, $R_4$ and $R_5$, independently of one another, are H, halogen, $CF_3$ or small alkyl group having from one to three carbon atoms. In particular, compounds of formula I having the ($\alpha S,\gamma S$) configuration or ($\alpha R,\gamma R$) configuration when $R_A$ or $R_B$ is a halogen are more potent inhibitors of kynureninase. Inhibitors of mammalian kynureninase are of particular use in therapy for certain neurological disorders.

14 Claims, No Drawings

INHIBITORS OF KYNURENINASE

This invention was made through a grant from the National Institutes of Health. The United States Government has certain rights in this invention.

BACKGROUND OF THE INVENTION

Kynureninases are a group of pyridoxal-5'-phosphate dependent enzymes which catalyze the hydrolytic β,γ-cleavage of aryl-substituted α-amino-γ-keto acids, particularly L-kynurenine or 3-hydroxyl-L-kynurenine to give L-alanine and anthranilic acid or 3-hydroxyanthranilic acid, respectively (see: K. Soda and K. Tanizawa (1979)Advances Enzym. 49:1–40). Kynureninase is involved in the microbial catabolism of L-tryptophan via the aromatic pathway. In plants and animals, a kynureninase is required in tryptophan catabolism and for NAD biosynthesis via quinolinic acid. Quinolinic acid is a relatively toxic metabolite which has been implicated in the etiology of neurological disorders, including epilepsy and Huntington's chorea (R. Schwarcz et al. (1988) Proc. Natl. Acad. Sci. USA 85:4079; M. F. Beal et al. (1986) Nature 321:168–171; S. Mazzari et al. (1986) Brain Research 380:309–316; H. Baran and R. Schwarcz (1990) J. Neurochem. 55:738–744). Inhibitors of kynureninase are thus important targets for treatment of such neurological disorders.

L-kynurenine (which can also be designated α,2-diamino-γoxobenzenebutanoic acid) is the preferred substrate of bacterial kynureninase, which is exemplified by that of *Pseudomonas fluorescens* (O. Hayaishi and R. Y. Stanier (1952) J. Biol Chem. 195:735–740). The kynureninase of tryptophan metabolism in plants and animals has a somewhat different substrate specificity with 3-hydroxy-L-kynurenine (which can be designated α,2-diamino-3-hydroxy-γ-oxobenzenebutanoic acid) being the preferred substrate (Soda and Tanizawa (1979) supra).

The mechanism of kynureninases has been the subject of considerable interest due to the unique nature of this pyridoxal-5'-phosphate dependent reaction. Mechanisms based on redox reactions ((J. B. Longenecker and E. E. Snell (1955) J. Biol. Chem. 213:229–235) or transamination (C. E. Dalgleish et al. (1951) Nature 168:20–22) have been proposed. More recently mechanisms involving either a nucleophilic mechanism with an "acyl-enzyme" intermediate (C. Walsh (1979) "Enzymatic Reaction Mechanisms" W. H. Freeman and Co., San Francisco, p. 821; M. Akhtar et al. (1984) "The Chemistry of Enzyme Action" New Comprehensive Biochemistry, Vol. 6 (M. I. Page, ed.) Elsevier, New York, p.821) or a general base-catalyzed mechanism (K. Tanizawa and K. Soda (1979) J. Biochem. (Tokyo) 86:1199–1209) have been proposed.

In addition to the physiological reaction, kynureninase has been shown to catalyze an aldol-type condensation of benzaldehyde with incipient L-alanine formed from L-kynurenine to give α-amino-γ-hydroxy-γ-phenylbutanoic acid (G. S. Bild and J. C. Morris (1984) Arch. Biochem. Biophys. 235:41–47). The stereochemistry of the product at the γ-position was not determined, although the authors suggested that only a single isomer was formed.

J. L. Stevens (1985) J. Biol Chem 260:7945–7950 reports that rat liver kynureninase displays cysteine conjugate β-lyase activity. This enzyme activity is associated with cleavage of S-cysteine conjugates of certain xenobiotics to give pyruvate, ammonia and a thiol, for example, cleavage of S-2-(benzothiazolyl)-L-cysteine to give 2-mercaptobenzothiazole, pyruvate and ammonia.

Several reports concerning the relative reactivities of kynurenine analogs with bacterial kynureninase or rat liver kynureninase are summarized in Soda and Tanizawa (1979) supra. Tanizawa and Soda (1979) supra reported that a number of ring substituted L-kynurenines, namely: 3-hydroxy-, 5-hydroxy-, 5-methyl-, 4-fluoro-, and 5-fluoroL-kynurenine were substrates of kynureninase of *P. fluorescens*. These authors also reported that dihydrokynurenine (called γ-(o-aminophenyl)-L-homoserine therein) was a substrate for that kynureninase, yielding oaminobenzaldehyde and L-alanine. The $K_m$ of dihydrokynurenine was reported to be 67 μM compared to a $K_m$ of 35 μM for L-kynurenine and 200 μM for 3-hydroxy-L-kynurenine. N'-formyl-L-kynurenine and β-benzoyl-L-alanine were likewise reported to be substrates (with $K_m$ =2.2 mM and 0.16 mM, respectively) for the bacterial kynureninase Tanizawa and Soda measured relative reactivity as relative amounts of L-alanine formed.

O. Hayaishi (1955) in "A Symposium on Amino Acid Metabolism" (W. D. McElroy and H. B. Glass, eds.) Johns Hopkins Press, Baltimore pp. 914–929 reported that 3-hydroxy- and 5-hydroxy-L-kynurenine, β-benzoyl-L-alanine and β-(o-hydroxybenzoyl)-L-alanine were substrates for the bacterial enzyme, but that N'-formyl-L-kynurenine was not a substrate. O. Hayaishi measured relative reactivities by determining the amount of substrate hydrolyzed.

Tanizawa and Soda (1979) supra reported that Sbenzoyl-L-cysteine, L-asparagine and D-kynurenine were not substrates of kynureninase, while O. Hayaishi (1955) supra reported that β-(p-aminobenzoyl)-L-alanine, β-(onitrobenzoyl)-L-alanine, β-(m-hydroxybenzoyl)-L-alanine, 3-methoxy-L-kynurenine, β-benzoylpropanoic acid, and β-(oaminobenzoyl)propanoic acid do not react with bacterial kynureninase. Kynureninase is reported to act only on Lamino acids (M. Moriguchi et al. (1973) Biochemistry 2:2969–2974).

O. Wiss and H. Fuchs (1950) Experientia 6:472 (see: Soda and Tanizawa (1979) supra) reported that 3-hydroxy-Lkynurenine, L-kynurenine, β-benzoyl-L-alanine, γ-phenyl-Lhomoserine, γ-methyl-L-homoserine, 2-aminolevulinic acid and α-amino-γ-hydroxypentanoic acid reacted with rat liver kynureninase to produce alanine, while β-(o-nitrobenzoyl)L-alanine did not.

G. M. Kishore (1984) J. Biol. Chem. 259:10669–10674 has reported that certain β-substituted amino acids are mechanism-based inactivators of bacterial kynureninase. Several β-substituted amino acids including: β-chloro-L-alanine, O-acetyl-L-serine, L-serine O-sulfate, S-(onitrophenyl)-L-cysteine and β-cyano-L-alanine inactivated kynureninase. These β-substituted amino acids react with kynureninase to give pyruvate and ammonia. However, a portion of the turnovers of the enzyme lead to formation of an inactive enzyme complex. L-S-(o-nitrophenyl)-L-cysteine was described as the "most efficient suicide substrate at low concentrations" with a $K_i$ of 0.1 mM.

Bacterial kynureninase is also strongly inhibited by o-aminobenzaldehyde ($K_i$ =6.5 μM, non-competitive inhibition). Several other aromatics having "a carboxyl group on the benzene ring and an amino group at the orthoposition" including o-aminoacetophenone, anthranilic acid o-nitrobenzaldehyde and benzaldehyde were described as inhibitors (Tanizawa and Soda (1979) supra). It was suggested that inhibition relates to binding of the formyl group to the portion of the enzyme that serves as a binding site for the γ-carboxyl of kynurenine. Anthranilate and 3-hydroxanthranilate, the products of the kynureninase reaction, were also reported to inhibit the enzyme (Takeuchi et al. (1980) J. Biochem. (Tokyo) 88:987-994).

J. P. Whitten et al. (1989) Tetrahedron Letts. 30:3649-3652 reported the synthesis of 2,2-difluoro-abenzoyl alanine (α-amino-β,β-difluoro-γ-oxobenzene butanoic acid) which is said to be a "potential new inhibitor of kynureninase." Fluoroketone-containing peptides are described as capable of forming stable hydrates or hemiketals which are "thought to inhibit" proteolytic enzymes as analogs of a tetrahedral transition state. The difluoro compound is described as a competitive inhibitor of kynureninase, but no details of this inhibition are given in the reference.

The present work is based on a reexamination of the mechanism of kynureninase catalysis, in particular, through an investigation of the stereospecificity of the retroaldol reaction catalyzed by the enzyme. During the course of this work, the reactivity of dihydrokynurenine with kynureninase was found to be significantly different than had previously been reported. The result of these mechanism and reactivity studies was the identification of a class of potent kynureninase inhibitors. The present invention provides kynureninase inhibitors which were designed to be "transition-state analogue" inhibitors.

SUMMARY OF THE INVENTION

It is an object of the present invention to provide means and compositions for inhibition of kynureninase. The inhibitors of the present invention are derivatives of αamino-γ-hydroxy-γ-hydroxybenzene butanoic acids of the formula:

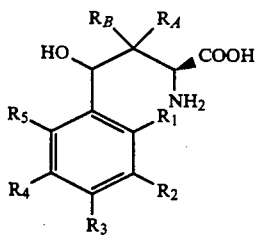

I wherein the stereochemical configuration at the α carbon is as indicated (the same configuration as L-kynurenine), wherein $R_a$ and $R_b$ independently of one another are H, halogen, $CF_3$ or a small alkyl group having one to three carbon atoms; $R_1$ is H, halogen, $NH_2$, $NR_6R_7$, $CF_3$ or a small alkyl group having from one to three carbon atoms, with $R_6$ and $R_7$, independently of one another, being H, $CH_3$ or COH, wherein only one of $R_6$ or $R_7$ can be COH; $R_2$ is OH, H, halogen, $CF_3$ or a small alkyl group having from one to three carbon atoms; and $R_3$, and $R_4$ and $R_5$, independently of one another, are H, OH, halogen, $CF_3$ or a small alkyl group having from one to three carbon atoms. It is preferred that the halogen is fluorine, that $R_2$ is H or OH that $R_1$ is $NH_2$ or H and that $R_A$, $R_B$, $R_3$, $R_4$ and $R_5$ are H or fluorine. It is more preferred that $R_1$ is $NH_2$ and that $R_A$, $R_B$, $R_3$, $R_4$ and $R_5$ are H.

For inhibition of bacterial kynureninase it is preferred that $R_1$ is $NH_2$. For inhibition of plant and animal kynureninase it is preferred that $R_1$ is $NH_2$ and $R_2$ is OH.

It is a further object of this invention to provide kynureninase inhibitors which are α-amino-γ-hydroxy-γ-aryl butanoic acids having the structure:

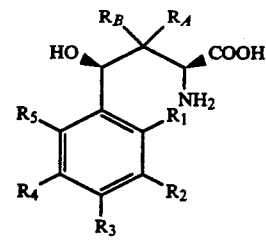

II wherein the stereochemical configuration at the α and γ carbons is as indicated and wherein $R_A$ and $R_B$, independently of one another, are H, halogen $CF_3$ or small alkyl group having one to three carbon atoms; $R_2$ is OH, H, halogen $CF_3$ or small alkyl having one to three carbon atoms; $R_1$ is $NH_2$, H, $NR_6R_7$, $CF_3$ or a small alkyl group having from one to three carbon atoms, wherein only one of $R_6$ or $P_7$ can be COH; $R_3$, $R_4$ and $R_5$ independently of one another are H, OH, halogen, $CF_3$ or a small alkyl group having from one to three carbon atoms The halogen is preferably F; $R_2$ is preferably H or OH; $R_1$ is preferably $NH_2$ or H and $R_A$, $R_B$, $R_3$, $R_4$ and $R_5$ are more preferably H. The stereoconfiguration of II at the α carbon is the same as in L-kynurenine. For inhibition of bacterial kynureninase it is preferred that $R_1$ is $NH_2$. For inhibition of plant and animal kynureninase it is preferred that $R_1$ is $NH_2$ and $R_3$ is OH.

Salts of the compounds of formulas I and II are considered functional equivalents thereof with respect to inhibition of kynureninase. In particular, pharmaceutically acceptable salts of the compounds of formulas I and II are useful for the methods of the present invention and are useful in any therapeutic treatment of animals based on the inhibitory action of the compounds of formulas I and II.

Inhibitors of the present invention include, among others, ring fluorinated dihydrokynurenines: (αS,γS)- or (αS,γR)-α,2-diamino-γ-hydroxy-4-fluorobenzenebutanoicacid, (αS,γS)- or (αS,γR) -α,2-diamino-γ-hydroxy-4-fluorobenzenebutanoic acid; ring hydroxylated dihydrokynurenines: (αS,γS)- or (αS,γR)-α,2-diamino-γ,5-dihydroxybenzenebutanoic acid; ring methylated dihydrokynurenines (αS,γR)- or (αS,γR)-α,2-diamino-γ-hydroxyl-5-methylbenzenebutanoic acid, or ring-substituted (αS,γS)- or (αS,γR)-α-amino-γ,2-dihydroxybenzenebutanoic acid.

Inhibitors of kynureninase also include dihydrokynurenines: (αS,γS) -α,2 -diamino-γhydroxybenzenebutanoic acid and (αS,γR)-α,γR)-α, 2-diaminol-γhydroxybenzenebutanoic acid; 3-hydroxydihydrokynurenines: (αS,γS)-α,2-diamino-γ,3-dihydroxybenzenebutanoic acid and (αS,γR)-α,2-diamino-γ,3-dihydroxylbenzenebutanoic acid and dihydrodesaminokynurenines: (αS,γS)-α-amino-γ-hydroxybenzenebutanoic acid and (αS,γR)-α-amino-γ-hydroxybenzenebutanoic acid. Dihydrokynurenine and dihydrodesaminokynurenine (see Soda and Tanizawa (I1979) supra p. 32, Table VIII) were previously reported to be substrates for certain kynureninases. Alternate substrates will act as competitive inhibitors toward the "natural" enzyme substrate. Dihydrokynurenine (Tanizawa and Soda (1979) supra) was reported to react readily with bacterial kynureninase with a reactivity about 65% that of Lkynurenine. The dihydrokynurenine employed in that reference was indicated to be a mixture of the ($\alpha$S,$\gamma$S) and ($\alpha$S,$\gamma$R) dihydrokynurenine diastereomers. It was not disclosed therein and the data given therein do not suggest that one of the diastereomers ($\alpha$S,$\gamma$S) is not a substrate for the kynureninase but acts as a competitive inhibitor of the enzyme for reaction of its natural substrates.

It is a further object of this invention to provide a method of inhibiting kynureninase in vitro and/or in vivo which comprises the step of contacting the enzyme with an inhibitory amount of one or more of the compounds of formulas I or II or salts, particularly pharmaceutically acceptable salts, thereof.

Therapeutic applications of the methods of the present invention relates particularly to inhibition of animal kynureninases, particularly those of mammals. Inhibitors in which $R_1$ is $NH_2$ and $R_2$ is OH are preferred for therapeutic applications.

Compounds of the present invention that are preferred for therapeutic applications of the methods of the present invention are those that have minimal toxic or irritant effect toward the target of the therapy. If the inhibitor reacts with kynureninase, it is important that the product of that reaction be substantially nontoxic.

Kynureninases from different sources have different substrate preferences. For example, the preferred substrate of mammalian kynureninase is 3-hydroxy-L-kynurenine rather than L-kynurenine. In general, for a particular kynureninase, a preferred inhibitor of formula I or II will possess the phenyl ring substitutions of a preferred substrate of that kynureninase.

DETAILED DESCRIPTION OF THE INVENTION

Kynureninases catalyze the hydrolysis of arylsubstituted $\gamma$-keto-$\alpha$-amino acids. Kynureninase has been identified and isolated from certain bacteria, fungi, yeasts as well as from mammalian sources. Kynureninases from different sources have been reported to have different substrate specificities. L-kynurenine is the preferred "natural" substrate of bacterial kynureninase. In contrast for mammalian, yeast and fungal kynureninases, 3-hydroxyL-kynurenine is the preferred "natural" substrate. This preference for 3-hydroxy-L-kynurenine, as assessed by relative substrate $K_m$'s, is characteristic of animal and plant kynureninase. The relative affinities of kynureninases for substrates other than L-kynurenine and 3-hydroxy-L-kynurenine can also depend on the source of the enzyme. Animal and plant kynureninases are sometimes called 3-hydroxykynureninases. The term kynureninase as used herein includes both bacterial, plant and animal kynureninases. Bacterial kynureninases are exemplified by the enzyme isolated from Pseudomonas fluorescens. Mammalian kynureninase is exemplified by the enzyme isolated from mammalian liver, in particular rat liver. A bacterial kynureninase will generally display substrate specificity like that of the P. fluorescens kynureninase. Mammalian kynureninase will generally display substrate specificity like that of rat liver kynureninase. Kynureninases, from all sources, catalyze the same types of reactions and so the mechanisms of the reactions they catalyze should be the same. Differences in affinities for substrates is believed to be associated with differences in the substrate binding site.

The present invention provides inhibitors of kynureninase. Some of these inhibitors are substrates of the enzyme, some are not substrates. Many of the inhibitors of this invention are competitive inhibitors of the enzyme for their natural substrates L-kynurenine and 3-hydroxy-L-kynurenine.

Inhibition, as used herein, refers to inhibition of the hydrolysis of L-kynurenine and 3-hydroxy-L-kynurenine. Competitive inhibition and noncompetitive inhibition can be assessed by in vitro methods well-known in the art. Preferred inhibitors of a particular kynureninase are those having a $K_i$ less than or equal to the $K_m$ of the preferred substrate either L-kynurenine or 3-hydroxy-L-kynurenine for that kynureninase. In general for competitive inhibitors, it is preferred that the inhibitor have an affinity equal to or greater than that of the preferred substrate for the enzyme. The level of inhibition that is achieved is dependent on the concentration of inhibitor in the vicinity of the enzyme. In general, the higher the affinity of the enzyme for the inhibitor, the more potent an inhibitor is. For applications of the methods of inhibition of kynureninase, particularly therapeutic applications, it is generally preferred to employ high affinity (low $K_i$) inhibitors to minimize the amount of inhibitor that must be administered.

Kynureninases are known to catalyze other reactions, for example, cysteine conjugate $\beta$-lyase activity. Inhibition of kynureninases can also be, at least qualitatively, assessed employing in vitro assays for such alternate kynureninase activities.

The aldol reaction of L-kynurenine and benzaldehyde catalyzed by kynureninase was found to proceed to give predominantly (80%) the ($\alpha$S, $\gamma$R) diastereomer of $\alpha$-amino-$\gamma$-hydroxybenzenebutanoic acid.

The stereospecificity of the aldol reaction, as well as the results of Bild and Morris, Arch. Biochem. Biophys. (1984) 235:41–47, supports a general base mechanism for kynureninase, as shown in Scheme 1. The stereospecificity for cleavage of the (4R)-isomer is likely a reflection of favorable orientation for the active site general base to initiate the retro-aldol cleavage by proton abstraction (Scheme 1A).

SCHEME I

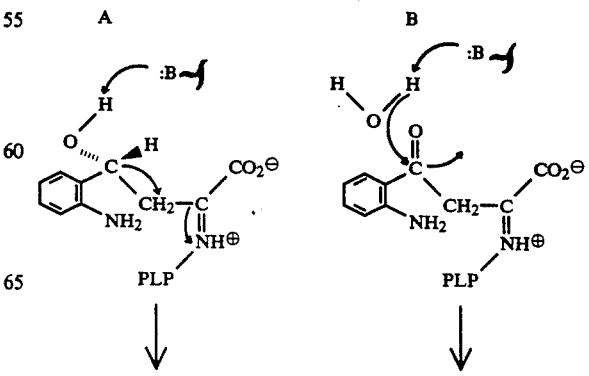

-continued
SCHEME I

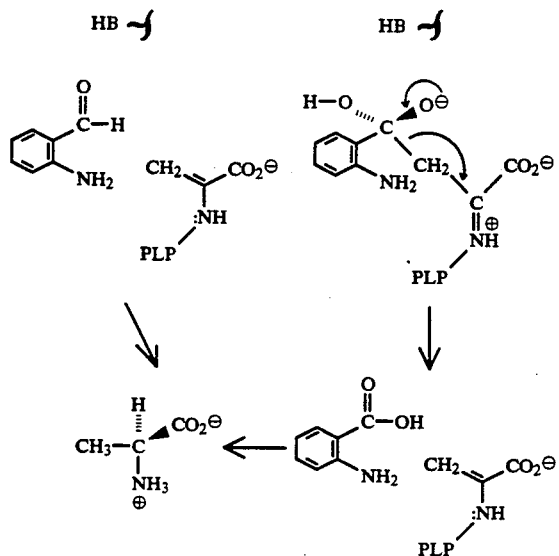

The basic group involved is probably the carboxylate that Kishore (1984) supra reported is modified by suicide substrate inhibitors. Although Kishore proposed that this carboxylate is responsible for α-proton abstraction, stereochemical studies by Palcic et al., J. Biol. Chem. (1985) 260:5248-5251, found that a α-proton of kynurenine is scrambled between the α and β-positions of the L-alanine product, and thus the proton abstraction at the α-C is probably due to a polyprotic base, most likely a lysine ε-amino group. In the hydrolysis of L-kynurenine, the second general base would be required to assist in hydration of the ketone, by abstraction of a proton from a water molecule (Scheme IB). The observed stereochemistry of the aldol-reactions suggests that the water attacks on the reface of the carbonyl group, giving the (S)-gem-diolate anion. Subsequent rapid collapse of this tetrahedral intermediate is likely and would generate the enzyme-bound enamine of PLP-L-alanine and anthranilic acid (Scheme 1B). In the case of the (4S)-isomer, the carbinol group would mimic this oem-diol tetrahedral intermediate, but is not oriented in a position favorable for the retro-aldol reaction to occur. Thus, this compound is a "transitionstate analogue," and would be expected to bind to kynureninase very tightly.

As an extension of these mechanistic studies, the reactivities of dihydrokynurenine diastereomers were examined (αS,γR)-Dihydrokynurenine (αS,γR)-α,2-diamino-γ-hydroxybenzenebutanoic acid) was found to be a slow substrate for the retro-aldol cleavage reaction catalyzed by kynureninase, while the analogous (αS,γS) diastereomer was unreactive. When these compounds were included in reaction mixtures of enzyme and L-kynurenine, the reaction was strongly inhibited. Analysis of the kinetic data in the presence of various concentrations of the dihydrokynurenines demonstrated that they act as competitive inhibitors with respect to kynurenine, and indicate that (αS,γS)-dihydrokynurenine binds more tightly than does L-kynurenine. This increased affinity of (αS,γS)-dihydrokynurenine is characteristic of mechanism-based, or "transition-state analogue" inhibitors.

The design of the kynureninase inhibitors of the present invention was based on the results of the inhibition studies on the diastereomers of dihydrokynurenine in combination with what is known of substrate specificity of kynureninases.

Although not wishing to be bound by any specific theory, it is believed that the inhibitors of the present invention represent "transition-state analogue" inhibitors of kynureninase in view of the newly proposed mechanism of Scheme I. Based on this proposed mechanism α-amino-γ-hydroxybenzenebutanoic acids having electron withdrawing groups including but not limited to $CF_3$, halogen, $NO_2$, CN etc. appropriately substituted on the benzene ring to stabilize the proposed "transition state" will act as inhibitors of the kynureninase.

The kynureninase inhibitors of the present invention can be prepared as exemplified for the preparation of the dihydrokynurenine diastereomers by selective reduction of the keto group of an appropriate γ-keto-amino acid or by other methods well known in the art. Kynurenines, including various ring-substituted kynurenines, can be prepared by ozonolysis of tryptophans. Alternatively, kynurenine analogs with desired ring substitution can be prepared enzymatically from appropriate tryptophans as described in Tanizawa and Soda (1979) supra and O. Hayaishi (1953) in Biochemical Preparations (E. E. Snell, ed.) Vol. 3, John Wiley & Sons, Inc., New York, pp. 108-111. The γ keto amino acid, β-benzoyl-DL-alanine can be prepared in several ways (for example, C. E. Dalgleish (1952) J. Chem. Soc. 137-141 and F. M. Verones ®®t al. (1969) Z. Naturforsch 24:294-300) including amination of β-benzoylacrylate (Tanizawa and Soda (1979) supra). β-Benzoyl alanines having various desired ring substitution can be prepared using analogous methods starting with appropriately substituted starting materials. Hayaishi (1955) supra and Wiss and Fuchs (1950) supra also provide sources of γ-keto amino acids useful for preparation of the compounds of the present invention. β-Benzoyl alanines can be selectively reduced by means known to the art to produce the inhibitors of the present invention.

Similarly, β-substituted γ-keto amino acids can serve as precursors to the β-(or 2-)substituted γ-hydroxy amino acids of the present invention. Whitten et al. (1990) supra, provides a synthesis of 2,2-difluoro-2-benzoyl alanine which can be selectively reduced to give α-aminoβ,β-difluoro-γ-hydroxybenzenebutanoic acid. Analogous methods can be employed to prepare β-substituted, phenylring substituted γ-hydroxybenzenebutanoic acids of the present invention.

As will be appreciated by those in the art, reduction of a chiral nonracemic γ-keto amino acid, preferably an L-amino acid, will generally result in a mixture of diastereomers. Techniques are available and well known in the art for the separation of diastereomers (HPLC, preparative TLC, etc.). As has been described herein, one of the pair of diastereomers will be a preferred kynureninase inhibitor. It will be appreciated, however, that inhibition can be obtained by use of a mixture of the diastereomers. In order to obtain maximal inhibition for the amount of inhibitor employed, it will be preferable to maximize the amount of the more inhibitory diastereomer in the mixture.

EXAMPLES

Example 1

Investigation of the Mechanism of Kynureninase-catalyzed adol-reactions.

Bacterial kynureninase was prepared from cells of *Pseudomonas fluorescene* (ATCC 11250, for example) essentially as described by Hayaishi and Stanier (1952) J. Biol. Chem. 195:735-740. Cells were grown on a minimal medium containing 0.1% L-tryptophan as the sole carbon and nitrogen source. L-kynurenine and benzaldehyde (in excess) were incubated with kynureninase under the conditions described by Bild and Morris (1984) Arch. Biochem. Biophys. 235:41-47, which is incorporated by reference herein. The product of this reaction was purified by preparative HPLC and identified as α-amino-γ-hydroxybenzenebutanoic acid. This product was produced in quantitative yield based on L-kynurenine.

The α-amino-γ-hydroxybenzenebutanoic acid produced in the kynureninase reaction exhibited a negative CD (circular dichroism) extremum at 260 nm, with vibronic splitting characteristic of a chirally substituted benzoyl alcohol chromophore. Based on a comparison of the CD spectra of the product with those of (R)- and (S)-mandelic acids, the predominant chiral product was determined to have the same absolute configuration as (S)-mandelic acid and thus to have the (γR)-configuration. (The terms R and S are employed as is conventional according to the Cahn-IngoldPrelog rules.) NMR analysis (300 MHz $^1$H) of the product demonstrates that it is an 80:20 mixture of (αS,γR):(αS,γS) diastereomers of α-amino-γ-hydroxybenzene butanoic acid.

Example 2

Reactivity of Dihydrokynurenine with Kynureninase.

L-kynurenine (from commercial sources) was reduced with NaBH$_4$ in H$_2$O to give dihydrokynurenine [α,2-diamino-γ-hydroxybenzenebutanoic acid]. The progress of reaction was monitored by the disappearance of the 360 nm UV absorption band of L-kynurenine. The reduction resulted in a 60:40 mixture of diastereomers. The diastereomers were separated by preparative HPLC on a 20×250 mm C18 column (Rainin, Dynamax) eluting with 0.1% acetic acid (5 ml/min). The first peak to elute from the HPLC column was identified by $^1$H NMR analysis to be the (αS,γS)-diastereomer. The second peak to elute was identified by $^1$H NMR analysis to be the (αS,γR)-diastereomer.

The CD spectra of the separated dihydrokynurenine diastereomers were consistent with this identification.

The reactivity of the two dihydrokynurenines with kynureninase in 0.1 M potassium phosphate buffer, pH 8.0, at 25 was examined. Reaction was followed by the appearance of o-aminobenzaldehyde, as determined spectrophotometrically by the increase in absorbance at 360 nm (See Tanizawa and Soda (1979) Biochem. (Tokyo) 86:1199-1209, which is incorporated by reference herein).

The (αS,γR)-dihydrokynurenine diastereomer reacted slowly with kynureninase to produce o-aminobenzaldehyde. No significant reaction of the (αS,γS)-diastereomer was detected. Tanizawa and Soda (1979) supra had reported that dihydrokynurenine reacted with kynureninase with a Vmax of about 65% that of L-kynurenine. In contrast, the present work indicates that only the (αS,γR)-diastereomer of dihydrokynurenine reacts, only at about 5% of the rate of L-kynurenine. Under the conditions employed and with the bacterial kynureninase prepared as described in Example 1, K$_m$ of the reaction of L-kynurenine was determined to be 25 μM. This value is similar to the K$_m$ of 35 μM for L-kynurenine obtained by Tanizawa and Soda.

Example 3

Inhibition of Kynureninase.

Inhibition of kynureninase was measured by including the potential inhibitor in the enzyme assay mixture (see Example 1 and Tanzawa and Soda (1979) supra) and determining the apparent Km for L-kynurenine (the preferred substrate of bacterial kynurenine) in the absence and presence of the potential inhibitor. H$_i$ values were then calculated using the standard equation:

$$(K_m)_{app} = K_m(1 + [I]/K_i)$$

where [I] is the molar concentration of inhibitor and K$_m$=25 μM.

Inhibition of kynureninase by the (αS,γR)- and (αS,γS)- diastereomers of dihydrokynurenine was examined and K$_i$'s were determined. Both compounds strongly inhibited the reaction of kynureninase with L-kynurenine. The K$_i$ value for the (αS,γS) diastereomer was lower than for the (αS,γR) diastereomer. Both compounds were found to be competitive inhibitors of kynureninase.

Inhibition of mammalian kynureninase can be measured using several different assays for enzyme activity. Rat liver kynureninase is obtained from homogenization of rat liver, followed by precipitation with (NH$_4$)$_2$SO$_4$, as described by Steven, J. L., J. Biol. Chem. (1985) 260:7945-7950, which is incorporated by reference herein. The activity of rat liver kynureninase was assessed by measurement of the cysteine conjugate β-lyase activity, as described by Stevens, with S-(2-benzothiazolyl)cysteine, a nonphysiological chromophoric substrate. Inhibition of kynureninase by the dihydrokynurenine diastereomers was assessed with respect to reaction with that substrate.

Both the (αS,γR) and (αS,γS) diastereomers of dihydrokynurenine were found to inhibit the reaction of rat liver kynureninase. The (αS,γS) diastereomer was found to be the stronger competitive inhibitor with K$_i$ under the assay conditions of about 690 μM.

We claim:

1. A compound selected from the group consisting of compounds having the formula:

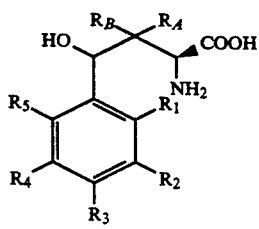

and pharmaceutically acceptable salts thereof, wherein:
R$_A$ and R$_B$, independently of one another are H, a halogen, CF$_3$ or a small alkyl group having one to three carbon atoms;

$R_1$ is $NH_2$, $NR_6R_7$, halogen, $CF_3$ or a small alkyl group having from one to three carbon atoms, wherein:

$R_6$ and $R_7$, independently of one another, are H, a formyl group or a small alkyl group having from one to three carbon atoms with the exception that only one of $R_6$ or $R_7$ can be a formyl group, $R_2$ is OH, halogen, or $CF_3$; and $R_3$, $R_4$ and $R_5$, independently of one another, are H, halogen, $CF_3$ or small alkyl group having from one to three carbon atoms.

2. The compound of claim 1 wherein said compound has the formula:

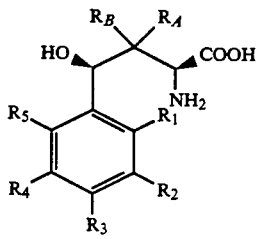

3. The compound of claim 1 wherein:

$R_A$ and $R_B$, independently of one another are H or F;

$R_1$ is $NH_2$ or F;

$R_2$ is OH or F; and $R_3$, $R_4$ and $R_5$, independently of one another, are H or F.

4. The compound of claim 3 wherein $R_1$ is $NH_2$.

5. The compound of claim 4 wherein $R_2$ is OH.

6. The compound of claim 3 wherein:

$R_A$, $R_B$, $R_3$, $R_4$ and $R_5$ are H;

$R_1$ is $MH_2$; and $R_2$ is OH.

7. A method for inhibiting kynureninase which comprises the step of contacting said kynureninase with an inhibitory amount of a compound selected from the group consisting of compounds having the formula:

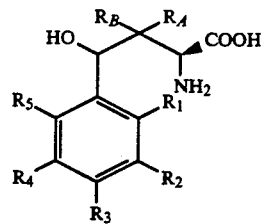

and pharmaceutically acceptable salts thereof, wherein:

$R_A$ and $R_B$, independently of one another are H, a halogen, $CF_3$ or a small alkyl group having one to three carbon atoms;

$R_1$ is $NH_2$, $NR_6R_7$, halogen, $CF_3$ or a small alkyl group having from one to three carbon atoms, wherein:

$R_6$ and $R_7$, independently of one another, are H, a formyl group or a small alkyl group having from one to three carbon atoms with the exception that only one of $R_6$ or $R_7$ can be a formyl group;

$R_2$ is OH, halogen, or $CF_3$; and $R_3$, $R_4$ and $R_5$, independently of one another, are H, halogen, $CF_3$ or small alkyl group having from one to three carbon atoms.

8. The method of claim 7 wherein said compound has the formula

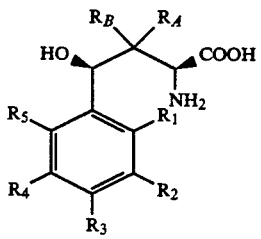

9. The method of claim 7 wherein:

$R_A$ and $R_B$, independently of one another are H or F;

$R_1$ is $NH_2$ or F;

$R_2$ is OH or F; and $R_3$, $R_4$ and $R_5$, independently of one another, are H or F.

10. The method of claim 9 wherein $R_1$ is $NH_2$.

11. The method of claim 9 wherein $R_2$ is OH.

12. The method of claim 10 wherein $R_2$ is OH.

13. The method of claim 7 wherein:

$R_A$, $R_B$, $R_3$, $R_4$ and $R_5$ are H;

$R_1$ is $NH_2$; and $R_2$ is OH.

14. The method of claim 7 wherein said kynureninase is a mammalian kynureninase and in said compound $R_1$ is $NH_2$ and $R_2$ is OH.

* * * * *

UNITED STATES PATENT AND TRADEMARK OFFICE
CERTIFICATE OF CORRECTION

PATENT NO. : 5,254,725

DATED : October 19, 1993

INVENTOR(S) : Phillips et al.

Page 1 of 2

It is certified that error appears in the above-indentified patent and that said Letters Patent is hereby corrected as shown below:

In column 2, line 15, delete "oaminobenzaldehyde" and replace with --o-aminobenzaldehyde--.
In column 2, line 33, delete "Sbenz-" and replace with --S-benz---.
In column 2, line 37, delete "(onitrobenzoyl)" and replace with --(o-nitrobenzoyl)--.
In column 2, line 41, delete "Lamino" and replace with --L-amino--.
In column 2, line 42, delete "2:" and replace with --12:--.
In column 2, line 46, delete "Lhomoserine" and replace with --L-homoserine--.
In column 2, line 55, delete "(onitrophenyl)" and replace with --o-nitrophenyl--.
In column 2, line 68, replace "acid" with --acid,--.
In column 3, line 11, delete "αbenzoyl" and replace with --α-benzoyl--.
In column 3, line 38, delete "αamino" and replace with --α-amino--.
In column 4, line 25, insert --with $R_6$ and $R_7$, independently of one another, being H, $CH_3$ or COH-- between "atoms," and "wherein".
In column 4, line 26, delete "$P_7$" and replace with --$R_7$--.
In column 4, line 35, delete "$R_3$" and replace with --$R_2$--.
In column 4, line 57, delete "γR)-α" and rewrite "2-diaminol-" as --2-diamino- --.
In column 4, line 66, delete "(I1979)" and replace with --(1979)--.
In column 5, line 4, delete "Lkynurenine" and replace with --L-kynurenine--.

UNITED STATES PATENT AND TRADEMARK OFFICE
CERTIFICATE OF CORRECTION

PATENT NO. : 5,254,725
DATED : October 19, 1993
INVENTOR(S) : Phillips et al.

It is certified that error appears in the above-indentified patent and that said Letters Patent is hereby corrected as shown below:

In column 7, line 45, delete "oem" and replace with --gem--.
In column 7, line 53, insert "." after "examined".
In column 7, line 62, insert --the data-- between "and" and "indicate".
In column 8, line 32, delete "® ®".
In column 8, line 48, delete "(I990)" and replace with --(1990).
In column 9, line 7, delete "*fluorescene*" and replace with --*fluorescens*--.
In column 9, line 14, delete "(I984)" and replace with --(1984)--.
In column 9, line 55, delete "25" and replace with --25°C--.
In column 11, line 48, delete "MH₂" and replace with --NH₂--.

Signed and Sealed this

Fifth Day of July, 1994

BRUCE LEHMAN

Attest:

*Attesting Officer*    *Commissioner of Patents and Trademarks*